United States Patent [19]

Huse et al.

[11] Patent Number: 5,378,359
[45] Date of Patent: Jan. 3, 1995

[54] PUSH COLUMN AND CHROMATOGRAPHY METHOD

[75] Inventors: William D. Huse, Del Mar; Anthony M. Sorge, La Jolla; Keith V. Sylvester, San Diego, all of Calif.

[73] Assignee: Strategene, La Jolla, Calif.

[21] Appl. No.: 827,995

[22] Filed: Jan. 30, 1992

Related U.S. Application Data

[63] Continuation of Ser. No. 292,808, Jan. 3, 1989, abandoned.

[51] Int. Cl.⁶ .............................................. B01D 15/08
[52] U.S. Cl. ........................... 210/198.2; 210/416.1; 210/635; 210/656; 422/70; 422/100; 422/101; 604/190
[58] Field of Search ................... 210/635, 656, 198.2, 210/416.1, 472; 604/187, 190, 191; 128/218; 436/161, 178; 422/70, 100, 101; 73/864.16, 864.17, 864.18, 864.81, 864.82, 864.83, 864.84, 864.85, 864.86, 864.87

[56] References Cited

U.S. PATENT DOCUMENTS

| | | | |
|---|---|---|---|
| 3,493,503 | 2/1970 | Mass | 604/190 |
| 3,810,545 | 5/1974 | Filz | 210/198.2 |
| 3,902,849 | 9/1975 | Barak | 210/198.2 |
| 4,138,474 | 2/1979 | Updike | 424/1 |
| 4,168,147 | 9/1979 | Acuff | 436/161 |
| 4,214,993 | 7/1980 | Forsythe | 210/198.2 |
| 4,270,921 | 6/1981 | Graas | 210/198.2 |
| 4,341,635 | 7/1982 | Golias | 210/198.2 |
| 4,388,272 | 6/1983 | Gesteland | 422/102 |
| 4,414,857 | 11/1983 | Brazhnikov et al. | 73/863.11 |
| 4,732,672 | 3/1988 | Kiang | 210/198.2 |
| 4,750,373 | 6/1988 | Shapiro | 73/864.87 |
| 4,766,082 | 8/1988 | Marteau D'Autry | 436/178 |
| 4,787,971 | 11/1988 | Donald | 210/198.2 |
| 4,929,427 | 5/1990 | Guala | 422/100 |
| 5,186,839 | 3/1993 | Kimura | 210/656 |

FOREIGN PATENT DOCUMENTS

| | | | |
|---|---|---|---|
| 2115717A | 9/1983 | United Kingdom | 210/198.2 |
| WO89/12229 | 12/1989 | WIPO | 210/198.2 |

OTHER PUBLICATIONS

Lehninger, "The Molecular Basis Of Cell Structure And Function"; Biochemistry, 2nd Edition; The Johns Hopkins University, School of Medicine; pp. 158–161.
Manlatis, et al., "The Molecular Cloning, A Laboratory Manual" Cold Spring Harbor Laboratory 1982; pp. 109–112, 197–199, 464–467.
Derwent WPI Abstract of S.U. Patent 1,182,385 dated Sep. 30, 1985, single page reference.

*Primary Examiner*—Ernest G. Therkorn
*Attorney, Agent, or Firm*—Limbach & Limbach

[57] ABSTRACT

An apparatus for chromatography of DNA, RNA, proteins and other molecules includes the use of a column adapted to hold a chromatography material and a sample to be filtered. A pneumatic pressure differential is applied across the column and the sample is urged through the chromatography material. A selected portion of the sample may then be collected.

11 Claims, 2 Drawing Sheets

PUSH COLUMN AND CHROMATOGRAPHY METHOD

This application is a continuation of U.S. patent application Ser. No. 07/292,808, filed Jan. 3, 1989, now abandoned.

BACKGROUND OF THE INVENTION

1. Field of the Invention

The present invention relates to an apparatus and methodology for the chromatography of materials, and in particular, chromatography based on molecular size, affinity and the like as used, for example, in the purification, separation or isolation of DNA and RNA fragments, proteins and other molecules.

2. Background Art

Removing unincorporated nucleotides from DNA and RNA fragments, isolating RNA fractions, purifying proteins and other macromolecules, are important procedures having a variety of applications. In DNA and RNA synthesis, unincorporated nucleotides must often be removed when constructing nick-translated probes, RNA probes and end-labeled oligonucleotides, as well as "filled-in" DNA fragments. It is important to separate the unincorporated free-nucleotides from the labeled probe as unincorporated label may bind to the solid support, resulting in unacceptably high levels of background noise. Isolation of RNA fractions may be employed in the separation of, for example, polyadenylated RNA from nonpolyadenylated RNAs. The use of chromatography methods to isolate and identify proteins and other macromolecules is another well known application.

Current chromatography methods, used particularly in connection with DNA and RNA synthesis, include ion-exchange chromatography, several variations of gel chromatography and others. Each has its own disadvantages. For example, ion-exchange methods require a number of steps which may result in a significant investment of time and, in the case of radiolabeled nucleotide filtering, extensive handling of radioactive material. Conventional gel-chromatography "drip" columns are tedious, requiring time to both pour and run. Spin columns, a variation of the "drip" column, are somewhat faster, but risk radiation exposure and contamination in the case of radionucleotide chromatography, and may yield less reliable results.

An alternative chromatography approach which avoids the aforementioned difficulties would therefore be desirable.

SUMMARY OF THE INVENTION

The present invention is directed to an apparatus and method for purifying, isolating and separating materials using gel chromatography. To that end, a chromatography material and a sample may be loaded into a column and pneumatic pressure applied to urge the sample through the chromatography material, whereby portions of the sample may be collected by the chromatography material and other portions excluded. In one embodiment, a positive pneumatic pressure is provided and in a second embodiment a negative pressure is applied. Additionally, a novel support structure may be employed to support the column during chromatography. The sample may thus be quickly and reliably treated.

DETAILED DESCRIPTION OF PREFERRED EMBODIMENTS

Figure 1:
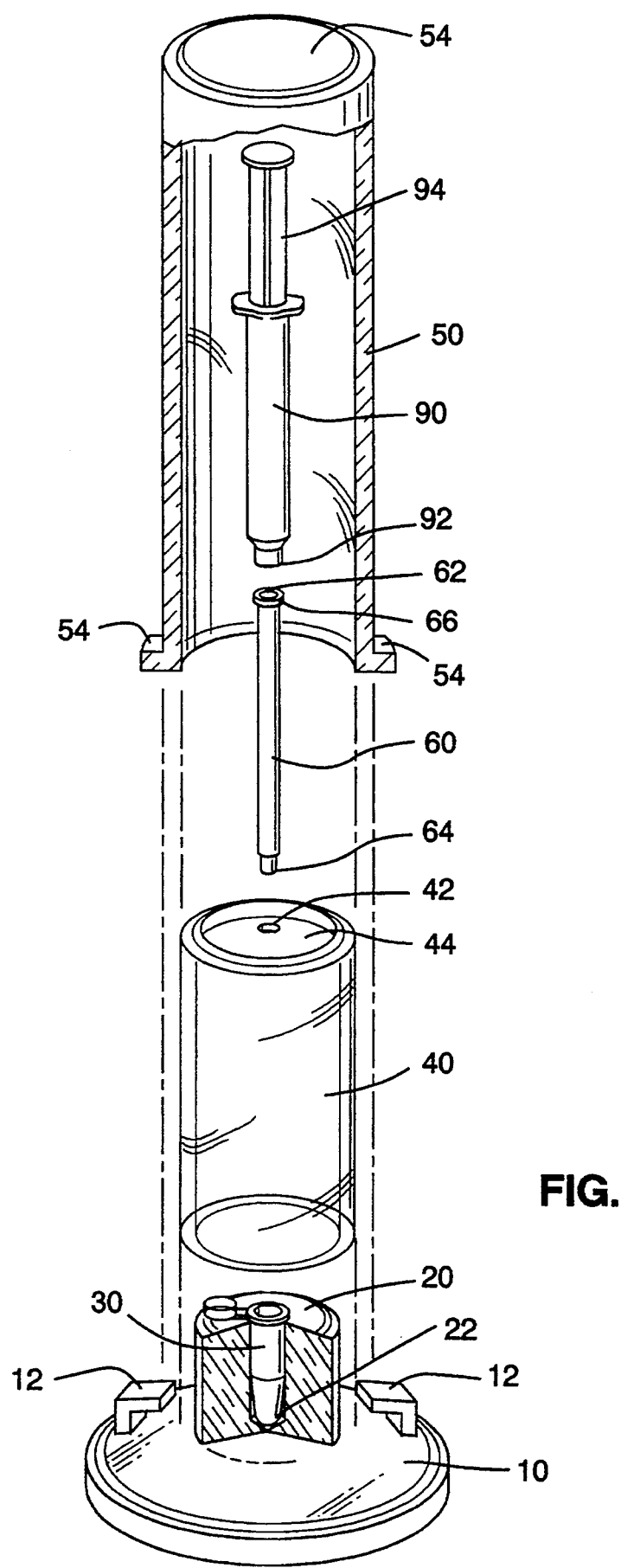
FIG. 1 is an exploded perspective view of an apparatus constructed in accordance with the present invention comprising a column, pressure inducing means, a collection vial and associated support structure.
Figure 2:
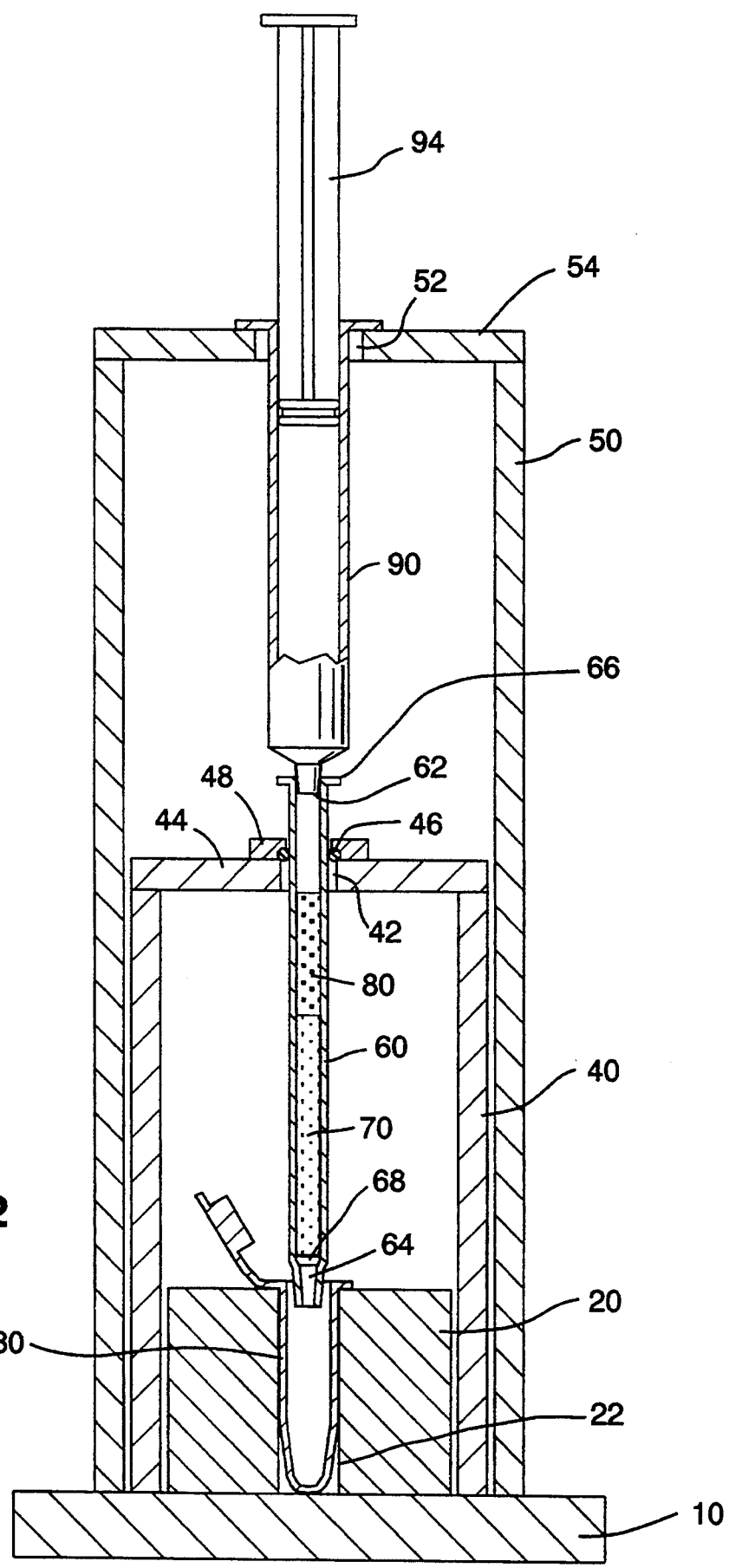
FIG. 2 is a cross-sectional view of the apparatus of FIG. 1 in a loaded position.

Referring to FIGS. 1 and 2, a chromatography apparatus constructed in accordance with the present invention comprises a generally disk shaped base 10 having a pair of retainers 12 and a generally cylindrical vial holding assembly 20 mounted thereon. Centrally located in the vial holding assembly 20 is a cylindrical chamber 22 for supporting a collection vial 30, into which the eluent from the column may be collected. The vial 30 may be a decapped Eppendorf tube or other suitable collection means. Removably mounted to the base 10, and slideably engaging the exterior wall of the vial holding assembly 20, is a generally cylindrical column support assembly 40. The column support assembly 40 includes a central aperture 42 formed in the generally planar upper surface 44 thereof. As shown in FIG. 2, the support assembly may have a resilient collar 46, such as an "O" ring or the like, positioned circumferentially adjacent the aperture 42, and a collar retainer 48 adapted to retain the collar 46 adjacent the aperture 42. Alternatively, as shown in FIG. 1, the collar 46 and the retainer 48 may be eliminated.

Optionally, a generally cylindrical pressure inducing means support assembly 50 may be removably mounted on the base 10. The support assembly may comprise a central aperture 52 formed in the generally planar upper surface 54 thereof, and is configured to slideably engage the exterior wall of the column support assembly 40. The aperture 52 is preferably axially aligned with the aperture 42 in the column support structure 40, which itself is preferably axially aligned with the chamber 22 in the vial holding assembly 20.

Alternatively, as shown in FIG. 1, the support assembly 50 may include an upper surface 54 having no aperture therein. The support assembly 50 may be further provided with a pair of locking tabs 54 adapted to engage the retainers 12 on the base 10 to lock the support assembly 50 in place during use. Other suitable locking mechanisms, such as threads, could also be employed. The assemblies 20, 40 and 50 may be formed of a radiation shielding material or, preferably, are constructed to fit securely inside a beta shield device. Molded plastic materials have been found suitable although other materials may also be employed.

Supported by the column holding assembly 40 above the vial 30 is a substantially tubular chromatography column 60. The column 60 may be about 1 ml in size, having a preferred internal diameter of about 5 mm and a preferred length of about 100 mm, and comprises openings 62 and 64, respectively, at each end thereof. An annular lip 66 may be provided circumferentially adjacent the upper opening 62, as shown in FIG. 1. The upper opening 62 is adapted to receive a chromatography material 70 and a sample 80 to be filtered. The lower opening 64 has an area of reduced cross-section adapted to prevent passage of the chromatography material 70 while permitting passage of the sample 80. Additionally, a screen or filter 68, comprising, for example, glass wool, may be employed to retain the chromatography material 70 within the column 60. Preferably, for a tubular column, the internal diameter should not exceed about 10 mm for most chromatography applications, lest the surface tension of the sample be insufficient to prevent effervescence and consequent loss of pressure through the sample. Increasing the length of the column 60 should enhance the degree of separation. Preferably, the column should be no less than about 60 mm in length.

Pneumatic pressure inducing means 90, in this case a syringe, may be attached to the upper opening 62 of the column 60. As shown in FIG. 1, the syringe 90 may include a series of threads 92 which engage the annular lip 66 of the column 60 to retain the column 60 and the syringe 90 in mutual engagement. In a first embodiment of the invention, the syringe 90, having the plunger 94 withdrawn as shown in FIG. 2, may be attached to the column 60 and a positive pneumatic pressure differential applied between the openings 62 and 64 of the column 60 by depressing the plunger. In that case, the support assembly 50 may be placed over the support assembly 40. As the assembly 50 is lowered, its upper surface 54 (if no aperture 52 is provided) will contact the plunger 94 and automatically depress same until the bottom of the support assembly 50 meets the base 10. At that point the support assembly 50 may be twisted until the locking tabs 54 mate with the retainers 12. If an aperture 52 is provided in the support assembly 50, the plunger 94 will extend therethrough and may be manually depressed. In an alternative embodiment, not shown, the pressure inducing means 90 may be attached to the lower opening 64 of the column (the column may be removed from the support assembly 40 in that case) and the sample drawn through the column by a negative pressure differential between the openings 62 and 64.

The chromatography procedure may be commenced by removing the column holding assembly 40 from the base 10 and inserting the collection vial 30 into the aperture 22 in the vial holding assembly 20. The column holding assembly 40 is then returned to the base 10. The column 60 is inserted into the aperture 42 in the column holding assembly 40 and positioned so that the lower end of the column extends into the collection vial 30. An appropriate chromatography material may then be introduced into the column 60 using the syringe 90, or other suitable means.

If unincorporated nucleotides are to be removed from DNA or RNA fragments, gel chromatography material such as a polysaccharide or polyacrylamide, having a selected degree of internal porosity, may be employed. The sample containing DNA or RNA fragments (large molecules) and unincorporated nucleotides (smaller molecules) may be introduced into the top of the column 40 using a suitable pipetting device. Capillary action draws the sample into the upper portion of the chromatography material, i.e., between the "beads" comprising the material as shown in FIG. 2. Preferably, if a 1 ml column is employed, about 10–50 ul, preferably 50 ul, and no more than about 200 ul, of sample may be introduced. With the column thus prepared, the syringe 90 may be attached with the plunger fully extended to the column 20. The plunger may then be firmly depressed (with or without use of the support assembly 50) until the sample is pushed through the column into the collection vial 30. If the support assembly 50 is employed, the support assembly locking mechanism can be actuated to retain the plunger in a fully depressed condition. As the sample proceeds through the chromatography material, the smaller molecules, for example, unincorporated nucleotides, are partitioned into the pores in the chromatography material while the large molecules, for example, DNA or RNA fragments, are excluded. The eluent from the column should be substantially free of unincorporated nucleotides.

A similar procedure may be employed for affinity chromatagraphy applications such as hybridization of complimentary strands of nucleic acids. For example, to separate polyadenylated RNA from nonpolyadenylated RNA, oligo(dT)-cellulose may be employed as a chromatography material. Under appropriate buffer conditions, the desired polyadenylated RNA will bind with the oligo (dT)-cellulose chromatography material while the nonpolyadenylated RNAs will be eluted into the collection vial 30. The polyadenylated RNA can be recovered by a second buffer condition. Other affinity chromatography applications include the purification of specific nucleic acid sequences, for example, viral genomic sequences, by generating complementary oligonucleotides.

Thus, an apparatus and chromatography method employing a pneumatic pressure differential have been disclosed. While embodiments and applications of this invention have been shown and described, it would be apparent to those skilled in the art that many more modifications are possible without departing from the inventive concepts herein. For example, although purification of DNA and RNA fragments and separation of polyadenylated from nonpolyadenylated RNAs has been disclosed, many other chromatography applications would be possible. The invention, therefore, is not to be restricted except in the spirit of the appended claims.

What is claimed is:

1. A push column comprising:
    a column adapted to hold a chromatography material and a sample, said column being substantially tubular and having lower and upper openings therein;
    a gel chromatography material residing in the column;
    a syringe attached to said upper opening of said column and having a plunger movable within the syringe for applying pressure to the chromatography material when the plunger is displaced;
    a collection vial positioned below the lower opening of said column; and
    a support structure having
        a base;
        a collection vial support coupled to the base and having a central chamber therein to support said vial;
        a column support adapted to slideably engage said vial support, said column support comprising an upper surface having an aperture therein adapted to support said column; and
        a syringe support adapted to slideably engage said column support, said syringe support comprising an upper surface adapted to engage said syringe.

2. The device of claim 1 further including a locking mechanism coupled between said syringe support and said base.

3. The apparatus as recited in claim 1 wherein said sample includes DNA or RNA fragments and unincorporated nucleotides, and wherein said gel chromatography material is either polysaccharide or polyacrylamide having internal porosity sufficient to absorb the unincorporated nucleotides and to exclude the DNA or RNA fragments.

4. The apparatus as recited in claim 1 wherein said sample includes polyadenylated RNA and non-polyadenylated RNA, and wherein said gel chromatography material is oligo (dT)-cellulose.

5. The apparatus as recited in claim 1 wherein said column has a volume of about 1 ml and said sample has a volume of at least about 10 ul.

6. The apparatus as recited in claim 1 wherein said column is a tube having a diameter no greater than 10 mm.

7. The apparatus as recited in claim 1 wherein said column support and said syringe support are composed of radiation shielding materials.

8. The apparatus as recited in claim 1 wherein the gel chromatography material is a resin adapted to absorb selected portions of a sample having a predetermined molecular size limit while excluding portions of said sample having a molecular size that exceeds said limit.

9. The apparatus as recited in claim 8 wherein the sample comprises DNA or RNA material having radiolabeled nucleotides incorporated therein and free radiolabeled nucleotides, and wherein the chromatography material is selected to absorb the free radiolabeled nucleotides and the DNA or RNA material is eluted from said column.

10. The apparatus as recited in claim 1 wherein the chromatography material separates a sample on the basis of affinity.

11. The apparatus as recited in claim 1 wherein the sample comprises a nucleic acid sequence and wherein the chromatography material comprises an oligonucleotide complimentary to the nucleic acid sequence.

* * * * *